United States Patent [19]

Cadwell

[11] Patent Number: 5,116,304

[45] Date of Patent: May 26, 1992

[54] MAGNETIC STIMULATOR WITH SKULLCAP-SHAPED COIL

[75] Inventor: John A. Cadwell, Kennewick, Wash.

[73] Assignee: Cadwell Industries, Inc., Kennewick, Wash.

[21] Appl. No.: 698,397

[22] Filed: May 10, 1991

Related U.S. Application Data

[60] Continuation-in-part of Ser. No. 548,025, Jul. 5, 1990, Pat. No. 5,047,005, Division of Ser. No. 8,210, Jan. 28, 1987, Pat. No. 4,940,453.

[51] Int. Cl.$^5$ ............................................. A61N 1/00
[52] U.S. Cl. ....................................... 600/13; 600/15
[58] Field of Search ................ 128/419 F, 731; 600/9, 600/11, 13, 14, 15

[56] References Cited

U.S. PATENT DOCUMENTS

| | | | |
|---|---|---|---|
| 735,581 | 8/1903 | Pollacsek et al. | 600/9 |
| 1,164,356 | 12/1915 | Kaiser | 600/9 |
| 2,808,826 | 10/1957 | Reiner et al. | 128/2.1 |
| 3,706,308 | 12/1972 | John et al. | 128/2.06 |
| 3,841,305 | 10/1974 | Hallgren | 128/1.3 |
| 3,841,306 | 10/1974 | Hallgren | 128/1.5 |
| 3,901,215 | 8/1975 | John | 128/2.1 |
| 3,915,151 | 10/1975 | Kraus | 128/1.5 |
| 4,056,097 | 11/1977 | Maass | 128/1.5 |
| 4,244,376 | 1/1981 | Fisher et al. | 128/731 |
| 4,304,242 | 12/1981 | Siarkiewicz et al. | 128/745 |
| 4,387,723 | 6/1983 | Atlee, III et al. | 128/734 |
| 4,408,616 | 10/1983 | Duffy et al. | 128/731 |
| 4,417,591 | 11/1983 | Culver | 128/731 |
| 4,454,883 | 6/1984 | Fellus | 128/422 |
| 4,493,327 | 1/1985 | Bergelson et al. | 128/731 |
| 4,493,539 | 1/1985 | Cannon, Jr. | 351/205 |
| 4,498,080 | 2/1985 | Culver | 340/728 |
| 4,570,640 | 2/1986 | Barsa | 128/741 |
| 4,595,018 | 6/1986 | Rantala | 128/733 |
| 4,641,633 | 2/1987 | Delgado | 128/1.3 |
| 4,665,920 | 5/1987 | Campbell | 128/422 |
| 4,672,951 | 6/1987 | Welch | 128/1.5 |
| 4,793,325 | 12/1988 | Cadossi et al. | 600/14 |
| 4,889,526 | 12/1989 | Rauscher et al. | 600/14 |
| 4,940,453 | 7/1990 | Cadwell | 600/13 |
| 4,977,896 | 12/1990 | Robinson et al. | 128/731 |
| 4,994,015 | 2/1991 | Cadwell | 600/13 |
| 5,000,178 | 3/1991 | Griffith | 600/13 |
| 5,030,196 | 7/1991 | Inoue | 600/14 |

OTHER PUBLICATIONS

A. T. Barker et al., "An Introduction to Magnetic Stimulation of the Human Brain and Peripheral Nervous System," Aug. 1985.

A. T. Barker et al., "Magnetic Stimulation of the Human Brain," *Physiological Society*, Jul. 1985, p. 9P.

Reginald G. Bickford, M.D., F.R.C.P., "Magnetic Stimulation of the Nervous System Nerve, Cord and Brain" (Grand Rounds Handout), Jul. 25, 1986.

(List continued on next page.)

*Primary Examiner*—Francis Jaworski
*Assistant Examiner*—George Manuel
*Attorney, Agent, or Firm*—Christensen, O'Connor, Johnson & Kindness

[57] ABSTRACT

A magnetic stimulator comprising a skullcap-shaped magnetic stimulator coil (13) connected to a suitable power supply (15) is disclosed. More specifically, the coil (13) is wound from bottom to top such that its shape defines a skullcap, i.e., a somewhat flat truncated cone with sides that curve slightly outwardly. While flexible enough to be coiled, the wire (21) used to create the coil has a relatively large AC carrying capacity for its size. The preferred wire is litz wire, or copper strip wire, i.e., wire that has a large periphery/cross-sectional area ratio. A layer of suitably soft material (23) is located on the inside of the coil (13) to provide a cushion between the coil and a human cranium (17) positioned beneath the coil (13). When triggered, the power supply produces sinusoidally fluctuating electrical power adequate to create a magnetic field suitable for stimulating the deeply located neurons (17) of a human cranium (17) positioned beneath the skullcap-shaped coil (13), i.e., adequate to create a neuron depolarizing electric field deeply within the cranium.

13 Claims, 1 Drawing Sheet

OTHER PUBLICATIONS

Reginald G. Bickford et al., "Neuronal Stimulation by Pulsed Magnetic Fields in Animals and Man," *Digest of the 6th International Conference on Medical Electronics and Biological Engineering*, Tokyo, 1965.

R. Jalinous et al., "The Design, Construction and Performance of a Magnetic Nerve Stimulator," *IEEE International Conference on Electric and Magnetic Fields in Medicine and Biology*, Dec. 1985, pp. 59–63.

"Non-Invasive Magnetic Stimulation of Human Motor Cortex," Sheffield University Note published in *The Lancet*, May 11, 1985.

Joachim A. Maass, "Contactless Nerve Stimulation and Signal Detection by Inductive Transducer," *IEEE Transactions on Magnetics, vol. MAG-6, No. 2, Jun. 1970, pp. 322–326.*

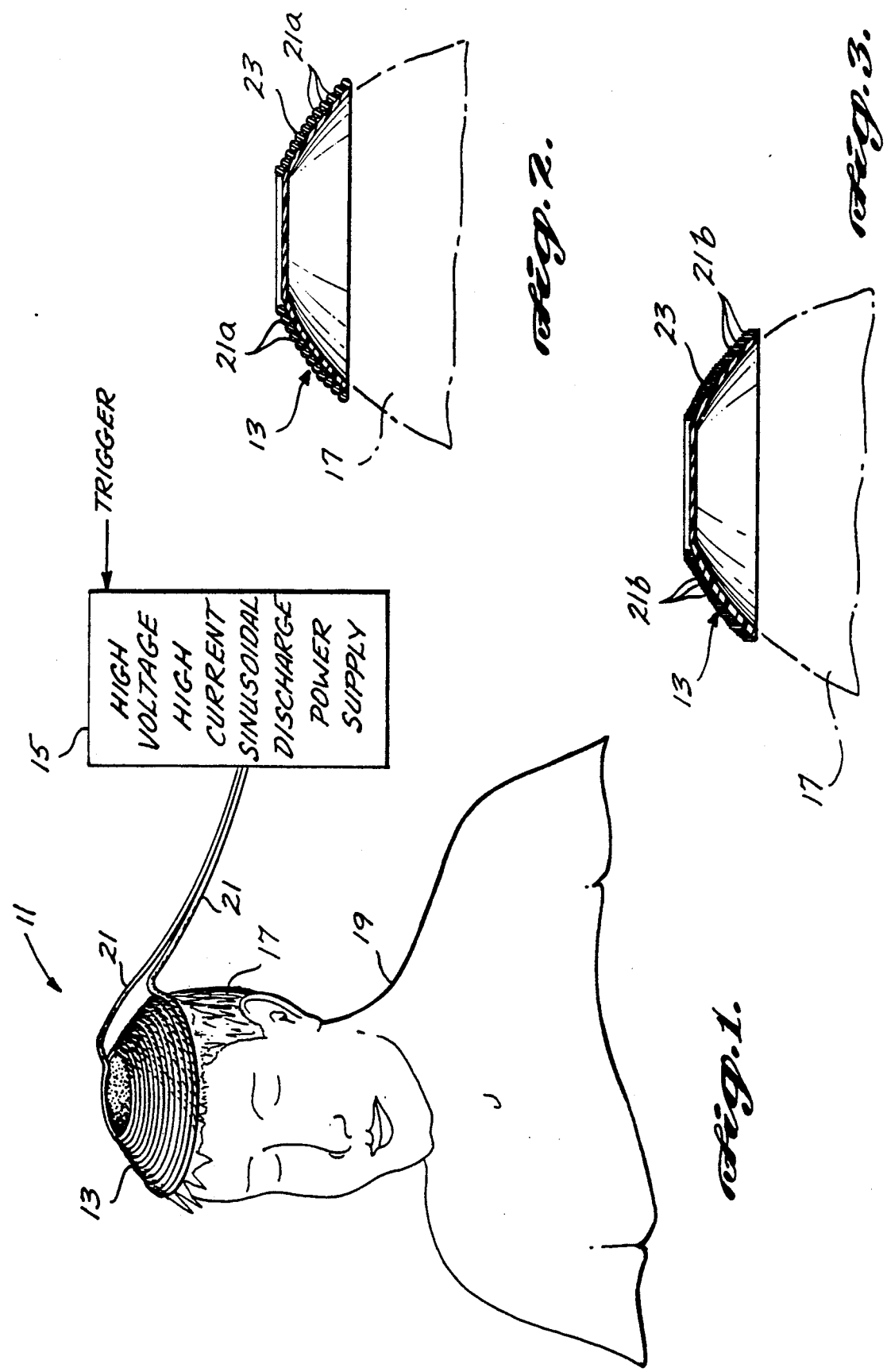

MAGNETIC STIMULATOR WITH SKULLCAP-SHAPED COIL

RELATIONSHIP TO OTHER APPLICATIONS

This application is a continuation-in-part of U.S. Pat. application Ser. No. 07/548,025, filed Jul. 5, 1990, now U.S. Pat. No. 5,047,005 and entitled METHOD AND APPARATUS FOR MAGNETICALLY STIMULATING NEURONS, which application is a division of U.S. application Ser. No. 07/009,210, now U.S. Pat. No. 4,940,453, filed Jan. 28, 1987, entitled METHOD AND APPARATUS FOR MAGNETICALLY STIMULATING NEURONS.

TECHNICAL AREA

This invention is directed to apparatus for stimulating the neural pathways of an organism and, more particularly, to stimulating the neural pathways of certain areas of higher level organisms, such as the cranium of the human body.

BACKGROUND OF THE INVENTION

As described in U.S. Pat. application Ser. No. 07/584,025, the subject matter of which is incorporated herein by reference, in recent years, methods and apparatus for creating evoked potentials in the neural pathways of higher level organisms (e.g., animals and humans) have been developed. Evoked potentials can produce observable movements and/or analyzable electrical signals (e.g., brain waves). Evoked potentials are created by stimulating neural pathways. One type of stimulator is an electrical stimulator. There are two types of electrical stimulators. One type is formed by a pair of spaced-apart electrodes. When electric potential is applied to the electrodes a current flow through the body is created. The current flow produces an electrical field that disrupts the polarization of neurons located in the field (commonly called depolarization of the neurons) causing an evoked potential "message" to be transmitted along the neural pathways formed by the depolarized and other neurons that define the neural pathway.

While electrical stimulation using a pair of spaced-apart electrodes has certain advantages, it has several disadvantages. One main disadvantage of electrode stimulation relates to the fact that the body is an insulator. As a result, the electrical current flow between the electrodes is shallow, i.e., it occurs near the skin. Because current flow is shallow, the electrical field created by the current flow is shallow. Thus, deep neurons are not depolarized and, thus not stimulated. While current can be increased to increase current penetration depth and, thus, stimulation depth, higher current flows cause pain and, thus, are undesirable. In fact, pain is one of the major reasons why the use of electrode stimulators to stimulate the brain can only be used on comatose patients. Awake patients generally cannot stand the pain associated with the high current flow needed to stimulate neurons enclosed by cranial bone.

In order to overcome the shallow penetration disadvantage of electrode stimulators, magnetic stimulators have been developed. Magnetic stimulators use a magnetic coil to create a neuron depolarizing magnetic field. Magnetic stimulators h ave the advantage of being relatively pain free and noncontacting, as well as being capable of stimulating deep and otherwise inaccessible neurons Depth is improved because, unlike current flow, body tissue does not resist magnetic flux. While magnetic stimulators have the ability to provide deeper penetration with less pain, as is best understood, neuron depolarization is still due to the creation of an electric field. More specifically, as best understood, the changing magnetic field created by a magnetic stimulator induces eddy currents in body tissue that, in turn, create a neuron depolarizing magnetic field.

While prior magnetic stimulators have been used to stimulate neurons in a relatively painless manner deeper than the neurons can be stimulated by electrode stimulators, the depth of penetration is still less than desired, particularly in the cranial area. The present invention is directed to providing a magnetic stimulator that is capable of stimulating deeper and otherwise inaccessible neurons in the cranial area.

SUMMARY OF THE INVENTION

In accordance with this invention, a magnetic stimulator formed by a skullcap-shaped magnetic stimulator coil and a suitable power supply is provided. More specifically, the invention comprises a coil wound from top to bottom such that its shape defines a skullcap. The coil is connected to a triggerable power supply that produces sinusoidal fluctuating AC power adequate to stimulate the neurons of a human cranium positioned beneath the skullcap-shaped coil.

In accordance with further aspects of this invention, the skullcap-shaped coil defines a somewhat flat truncated cone with sides that curve slightly outwardly.

In accordance with still other aspects of this invention, the coil is formed of wire having the capability of conductive relatively large alternating currents. The preferred wire is wire that has a large periphery/cross-sectional area ratio, i.e., a large periphery when compared to its cross-sectional area, such as litz wire or copper stripe wire.

In accordance with still further aspects of this invention, preferably a layer of a suitably soft material is located inside of the coil to provide a cushion between the coil and a human cranium positioned beneath the coil, and to thermally isolate the coil from the scalp to prevent burns.

As will be readily appreciated from the foregoing summary, the invention provides a magnetic stimulator suitable for stimulating neurons located deep within a human cranium. The skullcap shape of the magnetic stimulator coil creates a magnetic field that penetrates the cranium deer than do other coil shapes, such as flat coil shapes. The use of litz wire or copper strip wire, i.e., wire having a large periphery/cross-sectional area ratio, produces a relatively light-weight coil having high current carrying capability. In this regard, as will be better appreciated by reviewing application Ser. No. 07/548,025, the subject matter of which has been incorporated herein by reference, the sinusoidal voltage and current levels of the power applied to magnetic stimulator coils are relatively high for short periods of time. The frequency of the sinusoidal power is such that current tends to flow along the skin of the conductor carrying the current. This skin effect makes conductors having high periphery/cross-sectional area ratios more efficient that conductors having lower ratios. A more efficient conductor allows lower weight coils to be used without a loss of current carrying capability or depth of magnetic field penetration, and decreases heating of the coil.

BRIEF DESCRIPTION OF THE DRAWINGS

The foregoing and other features and advantages of the present invention will become better understood by reference to the following detailed description of a preferred embodiment o the invention when taken in conjunction with the accompanying drawings wherein:

FIG. 1 is a partially schematic and partially block diagram illustrating a magnetic stimulator formed in accordance with this invention;

FIG. 2 is a cross-sectional view of the skullcap-shaped magnetic stimulator coil illustrated in FIG. 1 formed of litz wire; and FIG. 3 is a cross-sectional view of the skullcap-shaped magnetic stimulator coil illustrated in FIG. 1 formed of copper strip wire.

DESCRIPTION OF THE PREFERRED EMBODIMENT

FIG. 1 illustrates a magnetic stimulator 11 formed in accordance with the invention. The magnetic stimulator comprises a skullcap-shaped coil 13 and a power supply 15. The skullcap-shaped coil 13 is illustrated in a position atop the cranium 17 of a patient 19.

As best shown in FIGS. 2 and 3, the skull-shaped magnetic stimulator coil 13 is wound from bottom to top such that its shape defines a skullcap (i.e., a wide-truncated cone with sides that curve slightly outwardly. Preferably, the wire used to wind the coil is litz wire 21a. Litz wire 21a consists of a number of separately insulated strands woven together so that each strand successively takes up all possible positions in the cross section of the entire conductor. This results in reduced skin effect and reduced radio frequency resistance. Alternatively, the coil could be formed of a copper wire strip 21b offset to create a skull shape. Like litz wire 21a, an insulated copper wire strip 21b has a large periphery/crosssectional area ratio.

The choice of wire is important because, as will be better understood from the following description, the current applied to the coil by the power supply 15 has a cycle period falling in the 50-300 microsecond range. As will be readily appreciated by those familiar with AC current flow, high-frequency currents pass trough the skin of a conductor, not the center. Choosing a conductor having a large periphery/cross-sectional area ratio maximizes the skin and, thus, minimizes the resistance to current flow for a conductor having a particular total weight. In summary, while conventional wires can be used to create an operable embodiment of the invention, litz wire and copper strip wire are preferred because of their better current carrying characteristics at the frequencies at which power is applied to the coil 13 by the power supply 15.

Preferably, a soft layer of material 23 is located beneath the skullcap-shaped coil 13. The soft layer 23 provides a cushion between the wire 21 that forms the coil 13 and the cranium 17 of the patient 19. Preferably, the soft layer 23 extends across the open top of the coil 13.

As illustrated in FIG. 1, the wire 21 that forms the coil 17 is connected to the output of the power supply 15. The power supply 15 is a triggerable high-voltage, high current sinusoidal discharge power supply, preferably of the type described in patent application Ser. No. 07/548,025, the subject matter of which has been incorporated herein by reference.

The frequency of the sinusoidally fluctuating electric power and, thus, the period of the magnetic field produced by the skullcap-shaped coil 13 is chosen to correspond to the time constant of the neurons to be stimulated. The current and voltage to the applied power are in phase quadrature with the current lagging the voltage. Preferably, during the first polarity (e.g., positive) excursion of the applied voltage, the magnetic field produced by the coil is insufficient to stimulate the underlying neurons, i.e., create a neuron depolarizing electric field. Rather, stimulation occurs during the second polarity (e.g., negative) excursion of the applied voltage. Preferably, coil current flow terminates at the end of the first cycle. Alternatively, if re-stimulation during the third and subsequent polarity excursions of the applied voltage is desired, the coil current can be allowed to decay.

As noted above, the power supply 15 is triggerable. Triggering can be created by the manual closing of a switch or by the receipt of a trigger pulse produced by a suitable device, such as in an evoked potential analyzer and recorder, as illustrated and described i U.S. Pat. application Ser. No. 07/548,025.

As will be readily appreciated from the foregoing description, the invention comprises a magnetic stimulator formed by a skullcap-shaped coil and a suitable power supply, i.e., a power supply that produces voltage and currents adequate to create a neuron depolarizing magnetic field when the skullcap-shaped coil is positioned atop the cranium of a patient. Preferably, the power supply is a sinusoidal discharge power supply. The presently preferred power supply is described in detail in parent application Ser. No. 07/548,025, subject matter of which is incorporated herein by reference.

While the skullcap-shaped coil is preferably formed of litz wire, as noted above, other types of wire can be used. Preferably, the chosen wire has a large periphery when compared to its cross-sectional area. A large periphery/crosssectional area ratio is desired because such wire has a reduced skin effect and, thereby, reduced radio frequency resistance. In this regard, in addition to litz wire, copper strip wire, such as 0.010 in. ×0.437 in. copper foil, meets this criteria. While large periphery/cross sectional ration wire is preferred, it is to be understood that the invention can also be practiced with regular wire, albeit with increased weight and reduced efficiency due to the increase in radio frequency resistance when compared to litz wire, copper strip wire and other wires having high periphery/cross-sectional area ratios.

With respect to the frequency of operation, as noted in parent application Ser. No. 07/548,025, the frequency of the power and, thus, the period of the magnetic field produced by the coil, is chosen to correspond to the time constant of the neurons to be stimulated. Usable magnetic field periods fall within the 50-300 microsecond range, which translates into frequencies in the 3,333-20,000 cps range. As will readily be understood by those skilled in the electronics art, this frequency range lies at the lower end and slightly below what is normally considered to be the radio frequency range of electromagnetic signals.

While a preferred embodiment of the invention has been illustrated and described, it will be appreciated that, within the scope of the appended claims, various changes can be made therein without departing from the spirit and scope of the invention.

The embodiments of the invention in which an exclusive property or privilege is claimed are defined as follows:

1. A magnetic stimulator comprising:
    a coil of wire wound into a skullcap shape and adapted for positioning on the cranium of a human being; and
    a power supply connected to said skullcap-shaped coil for applying power to said skullcap-shaped coil adequate to create a neuron depolarizing magnetic field when said skullcap-shaped coil is positioned on said cranium.

2. A magnetic stimulator as claimed in claim 1 wherein said skullcap-shaped coil defines a somewhat flat truncated cone with sides that curve outwardly.

3. A magnetic stimulator as claimed in claim 1 or 2 wherein said coil of wire has a large periphery/cross-sectional area ratio.

4. A magnetic stimulator as claimed in claim 3 wherein said coil wire is litz wire.

5. A magnetic stimulator as claimed in claim 4 including a layer of soft material located inside of said skullcap-shaped coil to provide a cushion between said skullcap-shaped coil and the cranium of a human being when said skullcap-shaped coil is positioned on the cranium of a human being.

6. A magnetic stimulator as claimed in claim 3 wherein said coil wire is copper strip wire.

7. A magnetic stimulator as claimed in claim 6 including a layer of soft material located inside of said skullcap-shaped coil to provide a cushion between said skullcap-shaped coil and the cranium of a human being when said skullcap-shaped coil is positioned on the cranium of a human being.

8. A magnetic stimulator coil adapted for positioning on the cranium of a human being and adapted for use in a magnetic stimulator to create a neuron depolarizing magnetic field, said magnetic stimulator coil comprising a coil of wire wound into a skullcap shape that defines a somewhat flat truncated cone with sides that curve outwardly.

9. A magnetic stimulator coil as claimed in claim 8 wherein said coil of wire has a large periphery/cross-sectional area ratio.

10. A magnetic stimulator coil as claimed in claim 9 wherein said coil wire is litz wire.

11. A magnetic stimulator coil as claimed in claim 10 including a layer of a soft material located inside of said skullcap-shaped coil to provide a cushion between said skullcap-shaped coil and a human cranium when said skullcap-shaped coil is positioned on the cranium of a human being.

12. A magnetic stimulator coil as claimed in claim 9 wherein said coil wire is copper strip wire.

13. A magnetic stimulator coil as claimed in claim 12 including a layer of a soft material located inside of said skullcap-shaped coil to provide a cushion between said skullcap-shaped coil and a human cranium when said skullcap-shaped coil is positioned on the cranium of a human being.

* * * * *

UNITED STATES PATENT AND TRADEMARK OFFICE
CERTIFICATE OF CORRECTION

PATENT NO. : 5,116,304
DATED : May 26, 1992
INVENTOR(S) : J.A. Cadwell It is certified that error appears in the above-identified patent and that said Letters Patent is hereby corrected as shown below:

| COLUMN | LINE | |
|---|---|---|
| 2 | 50 | "deer" should read --deeper-- |
| 3 | 25 | "skull-shaped" should read --skullcap-shaped-- |
| 3 | 44 | "trough" should read --through-- |
| 4 | 5 | "to" should read --of-- |
| 4 | 45 | "cross sectional ration" should read --cross-sectional ratio-- |

Signed and Sealed this

Seventh Day of September, 1993

*Attest:*

BRUCE LEHMAN

*Attesting Officer*  *Commissioner of Patents and Trademarks*